US007723295B2

(12) United States Patent
MacDonald et al.

(10) Patent No.: US 7,723,295 B2
(45) Date of Patent: *May 25, 2010

(54) PEPTIDES AND COMPOUNDS THAT BIND TO A RECEPTOR

(75) Inventors: Brian R. MacDonald, Newtown Square, PA (US); Jeffery Kenneth Weis, Whitehouse Station, NJ (US); Edward John Yurkow, Hillsborough, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 952 days.

This patent is subject to a terminal disclaimer.

(21) Appl. No.: 11/200,416

(22) Filed: Aug. 9, 2005

(65) Prior Publication Data

US 2006/0040866 A1 Feb. 23, 2006

Related U.S. Application Data

(63) Continuation-in-part of application No. 10/918,561, filed on Aug. 13, 2004.

(60) Provisional application No. 60/498,740, filed on Aug. 28, 2003.

(51) Int. Cl.
*A61K 38/00* (2006.01)
*A61K 39/00* (2006.01)
*C07K 5/00* (2006.01)
*C07K 7/00* (2006.01)

(52) U.S. Cl. .................. 514/3; 514/2; 514/13; 514/14; 514/15; 514/17; 530/300; 530/324; 530/325; 530/326; 530/327

(58) Field of Classification Search ........................ None
See application file for complete search history.

(56) References Cited

U.S. PATENT DOCUMENTS

| 5,141,851 | A | 8/1992 | Brown et al. |
|---|---|---|---|
| 5,143,854 | A | 9/1992 | Pirrung et al. |
| 5,270,170 | A | 12/1993 | Schatz et al. |
| 5,326,558 | A | 7/1994 | Turner et al. |
| 5,338,665 | A | 8/1994 | Schatz et al. |
| 5,358,934 | A | 10/1994 | Borovsky et al. |
| 5,384,331 | A | 1/1995 | Kogan et al. |
| 5,411,942 | A | 5/1995 | Widmer et al. |
| 5,869,451 | A | 2/1999 | Dower et al. |
| 5,932,546 | A | 8/1999 | Barrett et al. |
| 6,060,052 | A | 5/2000 | Murray et al. |
| 6,083,913 | A | 7/2000 | Dower et al. |
| 6,251,864 | B1 * | 6/2001 | Dower et al. ................... 514/13 |
| 2005/0282277 | A1 * | 12/2005 | MacDonald et al. ........ 435/372 |

FOREIGN PATENT DOCUMENTS

| EP | 668352 | 8/1995 |
|---|---|---|
| EP | 675201 | 10/1995 |
| EP | 0 450 715 B1 | 12/1995 |
| EP | 690127 | 1/1996 |
| EP | 0 783 003 B1 | 11/2006 |
| GB | 2285446 | 7/1995 |
| WO | WO 1990015070 | 12/1990 |
| WO | WO 1991007988 | 6/1991 |
| WO | WO 1991008752 | 6/1991 |
| WO | WO 1993025221 | 12/1993 |
| WO | WO 1995011922 | 5/1995 |
| WO | WO 1995018858 | 7/1995 |
| WO | WO 1995021626 | 8/1995 |
| WO | WO 1995021919 | 8/1995 |
| WO | WO 1995021920 | 8/1995 |
| WO | WO 1995028907 | 11/1995 |
| WO | WO 1996017062 | 6/1996 |
| WO | WO 96/34016 | 10/1996 |
| WO | WO 1996040750 | 12/1996 |
| WO | WO 1998025965 | 6/1998 |
| WO | WO 2001021180 | 3/2001 |
| WO | WO 02/78612 | 4/2003 |
| WO | WO 2004/026332 A | 4/2004 |
| WO | WO 2005/023834 A2 | 3/2005 |

OTHER PUBLICATIONS

Prochazka Z and Slaninova J, "The 1- and 2-Naphthylalanine analogs of Oxytocin and Vasopressin", Collect. Czech. Chem. Commun. 1995, 60: 2170-2177.*

International Search Report dated Mar. 15, 2007 for corresponding Appln. No. PCT/US2006/030359.

Case B.C., et al.: "The pharmacokinetics and pharmacodynamics of GW395058, a peptide agonist of the thrombopoietin receptor, in the dog, a large-animal model of chemotherapy-induced thrombocytopenia" Stem Cells (Dayton Ohio) 2000 vol. 18, No. 5, pp. 360-365, XP002421199.

De Serres M. et al.: "Pharmacokinetics and hematological effects of the PEGylated thrombopoietin peptides mimetic GW395058 in rats and monkeys after intravenous or subcutaneous administration", Stem Cells (Dayton, Ohio) 1999 vol. 17, No. 6, pp. 316-326, XP002421200.

De Serres M. et al.: "Immunogenicity of thrombopoietin mimetic peptide GW395058 in BALB7c mice and New Zealand white rabbits evaluation of the potential for thrombopoietin neutralizing antibody production in man" Stem Cells, Alphamed Press, Dayton, OH, US, vol. 17, 1999, pp. 203-209, XP002230261.

Kaushansky K: "Hematopoietic growth factor mimetics" Annals of the New York Academy of Sciences Jun. 2001, vol. 938, pp. 131-138, XP002421201.

(Continued)

*Primary Examiner*—Anish Gupta
*Assistant Examiner*—Julie Ha
(74) *Attorney, Agent, or Firm*—Andrea Jo Kamage; Laura Donnelly

(57) ABSTRACT

Peptide compounds that bind to and activate the thrombopoietin receptor (c-mpl or TPO-R) or otherwise act as a TPO agonist are disclosed.

13 Claims, 8 Drawing Sheets

OTHER PUBLICATIONS

Renschler, M: "Synthetic peptide ligands of the antigen binding receptor induce programmed cell death in a human B-cell lymphoma", Immunology, vol. 91, pp. 3623-3627 (1994).

Singer S.C. et al: "Pegylated Thrombopoietin (TPO)-mimetic Peptides Bind Human to TPO receptor causing proliferation and maturation of megakaryocytes in vitro" Blood, vol. 92, No. 10, Nov. 15, 1998, p. 568A, XP009079489 & 40th Annual Meeting of the American Society of Hematology; Miami Beach, Florida, USA, Dec. 4-8, 1998.

Wrighton, N. et al: "Small Peptide Mimetics of Erthropoietin", Blood, vol. 88, No. 10 (Supp. 1), pp. 543-545 (1996).

Ballmaier et al. "c-mpl mutations are the cause of congenital amegakaryocytic thrombocytopenia", Blood, vol. 97, No. 1, pp. 139-146 (2001).

Barker et al. "Cyclic RGD Peptide Analogues as Antiplatelet Antithrombotics", J. Med. Chem. vol. 35, pp. 2040-2048 (1992).

Bartley et al. "Identification and Cloning of a Megakaryocyte Growth and Development Factor That Is a Ligand for the Cytokine Receptor Mpl", Cell, vol. 77, pp. 1117-1124 (1994).

Basser et al., "Randomized, Blinded, Placebo-Controlled Phase I Trail of Pegylated Recombinant Human Megakaryocyte Growth and Development Factor With Fiilgrastim After Dose-Intensive Chemotherapy in Patients With Advanced Cancer", Blood, vol. 89, No. 9, pp. 3118-3128 (1997).

Bazan et al. "Structural design and molecular evolution of a cytokine receptor superfamily", Proc Natl. Acad. Sci. USA, vol. 87, pp. 6934-6938 (1990).

Berger et al. "A New Method for the Synthesis of Optically Active [small alpha, Greek]-Amino Acids and Their N[small alpha, Greek] Derivatives via Acylamino Malonates", J. Org. Chem., vol. 38, No. 3, pp. 457-460 (1973).

Caras et al. "Signal Peptide for Protein Secretion Directing Glycophospholipid Membrane Anchor Attachment", Science, vol. 243, pp. 1196-1198 (1989).

Cwirla et al. "Peptides on Phage: A Vast Library of Peptides for Identifying Ligands", Proc. Natl. Acad. Sci. USA, vol. 87, pp. 6378-6382 (1990).

Daumas et al. "Gramicidin A analogs: influence of the substitution of the tryptophans by naphthylalanines", Biochimie, vol. 71, pp. 77-81 (1989).

De Sauvage et al. "Stimulation of megakaryocytopoiesis and thrombopoiesis by the c-Mpl ligand", Nature, vol. 369, pp. 533-538 (1994).

Dexter et al. "Growth of Factor-Dependent Hemopoietic Precursor Cell Lines", J. Exp. Med., vol. 152, pp. 1036-1047 (1980).

Dower et al. "The Search for Molecular Diversity (II): Recombinant and Synthetic Randomnized Peptide Libraries", Annual Reports in Medicinal Chemistry, vol. 26, pp. 271-280 (1991).

Dower et al. "High efficiency transformation of E. coli by high voltage electroporation", Nucleic Acids Research, vol. 16, No. 13, pp. 6127-6145 (1988).

Evans et al. "Design of Nonpeptidal Ligands for a Peptide Receptor: Cholecystokinin Antagonists", J. Med. Chem, vol. 30, pp. 1229-1239 (1987).

Fauchere "Elements for the Rational Design of Peptide Drugs", Advances in Drug Research, vol. 15, pp. 29-69 (1986).

Fodor et al. "Light-Directed, Spatially Addressable Parallel Chemical Synthesis", Science, vol. 251, pp. 767-773 (1991).

Fox et al. "Thrombopoietin expands hematopoietic stem cells after transplantation", The Journal of Clincal Investigation, vol. 110, No. 3, pp. 389-394 (2002).

Gante "Peptidomimetics-Tailored Enzyme Inhibitors", Angen. Chem. Int. Ed. Engl., vol. 33, pp. 1699-1720 (1994).

Harker "Kinetics of Thrombopoiesis", The Journal of Clinical Investigation, vol. 47, pp. 458-465 (1968).

Kato et al., "Purification and Characterization of ThrombopoietinI", J. Biochem. vol. 118, No. 1, pp. 229-236 (1995).

Kaushansky et al., "Promotion of megakaryocyte progenitor expansion and differentation by the c-Mpl ligand thrombopoietin", Nature, vol. 369, pp. 568-571 (1994).

Kaushansky et al., "Thrombopoietin Expands Erythroid Progenitors, Increases Red Cell Production, and Enhances Erythroid Recovery after Myelosuppressive Therapy", J. Clin. Invest., vol. 96, pp. 1683-1687 (1995).

Kaushansky et al., "Thrombopoietin expands erythroid, granulocyte-macrophage, and megakaryocytic progenitor cells in normal and myelosuppressed mice", Experimental Hematology, vol. 24, pp. 265-269 (1996).

Kimura et al. "Hematopoietic stem cell deficiencies in mice lacking c-Mpl, the receptor for thrombopoietin", Proc. Natl. Acad. Sci. USA, vol. 95, pp. 1195-1200 (1998).

Kojima et al. "Molecular Cloning and Expression of Megakaryocyte Potentiating Factor cDNA*", The Journal of Biological Chemistry, vol. 270, No. 37, pp. 21984-21990 (1995).

Ku et al. "Thrombopoietin, the Ligand for the Mpl Receptor, Synergizes With Steel Factor and Other Early Acting Cytokines in Supporting Proliferation of Primitive Hematopoietic Progenitors of Mice", Blood, vol. 87, No. 11, pp. 4544-4551 (1996).

Kuter et al. "The purification of megapoietin: A physiological regulator of megakaryocyte growth and platelet production", Proc. Nat. Acad. Sci. USA, vol. 91, pp. 11104-11108 (1994).

Mcdonald "Thrombopoietin, Its Biology, Clinical Aspects, and Possibilities" The American Journal of Pediatric Hematology/Oncology, vol. 14, No. 1, pp. 8-21 (1992).

Metcalf "Thrombopoietin-at last", Nature, vol. 369, pp. 519-520 (1994).

Methia "Oligodeoxynucleotides Antisense to the Proto-oncogene c-mpl Specifically Inhibit in Vitro Megakaryocytopoiesis", Blood, vol. 82, No. 5, pp. 1395-1401 (1993).

Mosmann "Rapid Colorimetric Assay for Cellular Growth and Survival: Application to Proliferation and Cytotoxicity Assays", Journal of Immunological Methods, vol. 65, pp. 55-63 (1983).

Neelis et al. "Prevention of Thrombocytopenia by Thrombopoietin iin Myelosuppressed Rhesus Monkeys Accompanied by Prominent Erythropoietic Stimulation and Iron Depletion", Blood, No. 90, No. 1, pp. 58-63 (1997).

Nestor et al. "Synthesis and Biological Activity of Some Very Hydrophobic Superagonist Analogues of Luteinizing Hormone-Releasing Hormone1", J. Med. Chem., vol. 25, pp. 795-801 (1982).

Or et al. "Cysteine Alkylation in Unprotected Peptides: Synthesis of a Carbavasopressin Analogue by Intramolecular Cysteine Alkylation", J. Org. Chem., vol. 56, pp. 3146-3149 (1991).

Papayannopoulou et al. "Insights into the cellular mechanisms of erythropoietin-thrombopoietin synergy", Experimental Hematology, vol. 24, pp. 660-669 (1996).

Porter et al. "Synthesis, resolution and characterization of ring substituted phenylalanines and tryptophans", International Journal of Peptide and Protein Research, vol. 30, No. 1 (Abstract). 1987. pp. 13-21.

Sitnicka et al. "The Effect of Thrombopoietin on the Proliferation and Differentation of Murine Hematopoietic Stem Cells", Blood, No. 87, No. 12, pp. 4998-5005 (1996).

Solar et al. "Role of c-mpl in Early Hematopoiesis", Blood, vol. 92, No. 1, pp. 4-10 (1998).

Souyri et al. "A Putative Truncated Cytokine Receptor Gene Transduced by the Myeloproliferative Leukemia Virus Immortalizes Hematopoietic Progenitors", Cell, vol. 63, pp. 1137-1147 (1990).

Veber et al. "The design of metabolically-stable peptide analogs", Trends in Neurosciences (TINS), pp. 392-396 (1985).

Vigon et al. "Molecular cloning and characterization of MPL, the human homolog of the v-mpl oncogene: Identification of a member of the hematopoietic growth factor receptor superfamily", Proc. Natl. Acad. Sci. USA, vol. 89, pp. 5640-5644 (1992).

Wada et al. "Characterization of the Truncated Thrombopoietin Variants", Biochemical and Biophysical Research Communications, vol. 213, No. 3, pp. 1091-1098 (1995).

Wang et al. "Design and synthesis of novel X2-constrained phenylanine, naphthylalanine, and tryptophan analogues and their use in biologically active melanotropin peptides", Tetrahedron, vol. 58, pp. 7365-7374 (2002).

Wendling et al. "The Oncongene V-MPL, A Putative Truncated Cytokine Receptor Which Immortalizes Hematopoietic Progenitors", L'Inserm, pp. 145-146 (1992).

Wendling et al. "c-Mpl ligand is a humoral regulator of megakaryocytopoiesis", Nature, pp. 571-574 (1994).

Yabe et al. "Analogues of Luteinizing Hormone-Releasing Hormone with Modification in Position 31)", Chem. Pharm. Bull., pp. 3149-3157 (1976).

Yabe et al. "Synthesis and Biological Activity of Tetragastrin Analogues modifying the Tryptophan Residue1)", Chem. Pharm. Bull., vol. 25, No. 10, pp. 2731-2734 (1977).

Yabe et al. "Synthesis and Biological Activity of Somatostatin Analogues modified at the Tryptophan Residue1)", Chem. Pharm. Bull., vol. 26, No. 3, pp. 993-997 (1978).

* cited by examiner

SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)
<223> OTHER INFORMATION: Variable amino acid

```
<400> SEQUENCE: 1

Trp Ser Xaa Trp Ser
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ala, Cys, Glu, Gly, Ile, Leu, Met, Pro, Arg,
      Gln, Ser, Thr, or Val, preferably Ala or Ile
<220> FEATURE:
<221> NAME/KEY: MOD_RES
<222> LOCATION: (2)
<223> OTHER INFORMATION: Ala, Cys, Asp, Glu, Lys, Leu, Gln, Arg, Ser,
      Thr, or Val, preferably Asp, Glu, or Lys
<220> FEATURE:
<221> NAME/KEY: MOD_RES
<222> LOCATION: (4)
<223> OTHER INFORMATION: Cys, Leu, Met, Pro, Gln, or Val
<220> FEATURE:
<221> NAME/KEY: MOD_RES
<222> LOCATION: (5)
<223> OTHER INFORMATION: Phe, Lys, Leu, Asn, Gln, Arg, Ser, Thr, or Val
<220> FEATURE:
<221> NAME/KEY: MOD_RES
<222> LOCATION: (6)
<223> OTHER INFORMATION: Cys, Phe, Ile, Leu, Met, Arg, Ser, Val, or Trp
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (8)
<223> OTHER INFORMATION: Ala, Asp, Glu, Gly, Lys, Met, Gln, Arg, Ser,
      Thr, Val, or Tyr
<220> FEATURE:
<221> NAME/KEY: MOD_RES
<222> LOCATION: (9)
<223> OTHER INFORMATION: 2-Nal
<220> FEATURE:
<221> NAME/KEY: MOD_RES
<222> LOCATION: (10)
<223> OTHER INFORMATION: Cys, Gly, Ile, Lys, Leu, Met, Asn, Arg, or Val

<400> SEQUENCE: 2

Xaa Xaa Gly Xaa Xaa Xaa Xaa Xaa Xaa Xaa
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: 2-Nal
<220> FEATURE:
<221> NAME/KEY: MOD_RES
<222> LOCATION: (14)
<223> OTHER INFORMATION: Sar
```

```
<400> SEQUENCE: 3

Ile Glu Gly Pro Thr Leu Arg Gln Xaa Leu Ala Ala Arg Xaa
 1               5                  10
```

US 7,723,295 B2

PEPTIDES AND COMPOUNDS THAT BIND TO A RECEPTOR

CROSS REFERENCE TO RELATED APPLICATIONS

This application which is a continuation-in-part of U.S. application Ser. No. 10/918,561, filed on Aug. 13, 2004, claims priority to U.S. application Ser. No. 10/918,561 and 60/498,740, filed Aug. 28, 2003 the entire contents of which are incorporated herein by reference.

FIELD OF THE INVENTION

The present invention provides peptide compounds that bind to and activate the thrombopoietin receptor (c-mpl or TPO-R) or otherwise act as a TPO agonist. The invention has application in the fields of biochemistry and medicinal chemistry and particularly provides TPO agonists for use in the treatment of human disease.

BACKGROUND OF THE INVENTION

Megakaryocytes are bone marrow-derived cells, which are responsible for producing circulating blood platelets. Although comprising <0.25% of the bone marrow cells in most species, they have >10 times the volume of typical marrow cells. See Kuter, et. al., Proc. Natl. Acad. Sci. USA 91:11104-11108 (1994). Megakaryocytes undergo a process known as endomitosis whereby they replicate their nuclei but fail to undergo cell division and thereby give rise to polyploid cells. In response to a decreased platelet count, the endomitotic rate increases, higher ploidy megakaryocytes are formed, and the number of megakaryocytes may increase up to 3-fold. See Harker, J. Clin. Invest., 47:458-465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf, Nature, 369:519-520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Platelets (thrombocytes) are necessary for blood clotting. When their numbers are very low a patient is at serious risk of death from catastrophic hemorrhage. TPO therefore has potential useful application in both the diagnosis and the treatment of various hematological disorders, for example, diseases primarily due to platelet defects. Ongoing clinical trials with TPO have indicated that TPO can be administered safely to patients. In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. See, e.g., McDonald, Am. J. Ped. Hematology/Oncology, 14:8-21 (1992).

The gene encoding TPO has been cloned and characterized. See Kuter, et al., Proc. Natl. Acad. Sci. USA, 91:11104-11108 (1994); Barley, et al., Cell 77:1117-1124 (1994); Kaushansky et al., Nature 369:568-571 (1994); Wendling, et al., Nature, 369:571-574 (1994); and Sauvage et al., Nature 369:533-538 (1994). Thrombopoietin is a glycoprotein with at least two forms, with apparent molecular masses of 25 kDa and 31 kDa, with a common N-terminal amino acid sequence. See, Bartley, et al., Cell, 77:1117-1124 (1994). Thrombopoietin appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO-R (also known as c-mpl) have been described. See Vigon, et al., Proc. Natl. Acad. Sci. USA, 89:5640-5644 (1992). TPO-R is a member of the hematopoietin growth factor receptor family, a family characterized by a common structural design of the extracellular domain, including four conserved C residues in the N-terminal portion and a WSXWS motif (SEQ ID NO:1) close to the transmembrane region. See Bazan, Proc. Natl. Acad. Sci. USA, 87:6934-6938 (1990). Evidence that this receptor plays a functional role in hematopoiesis includes observations that its expression is restricted to spleen, bone marrow, or fetal liver in mice (see Souyri, et al., Cell 63:1137-1147 (1990)) and to megakaryocytes, platelets, and CD34+ cells in humans (see Methia, et al., Blood 82:1395-1401 (1993)). Furthermore, exposure of CD34+ cells to synthetic oligonucleotides antisense to mpl RNA significantly inhibits the appearance of megakaryocyte colonies without affecting erythroid or myeloid colony formation. Some workers postulate that the receptor functions as a homodimer, similar to the situation with the receptors for G-CSF and erythropoietin.

The availability of cloned genes for TPO-R facilitates the search for agonists of this important receptor. The availability of the recombinant receptor protein allows the study of receptor-ligand interaction in a variety of random and semi-random peptide diversity generation systems. These systems are disclosed in U.S. Pat. Nos. 6,251,864, 6,083,913, 6,121,238, 5,932,546, 5,869,451, 5,506,362, and 6,465,430 and in Cwirla et al., Proc. Natl. Acad. Sci. USA, 87:6378-6382 (1990); each of the foregoing patent applications and publications is incorporated herein by reference.

The slow recovery of platelet levels in patients suffering from thrombocytopenia is a serious problem, and has lent urgency to the search for a blood growth factor agonist able to accelerate platelet regeneration. The present invention provides such an agonist.

SUMMARY OF THE INVENTION

The present invention is directed to defined low molecular weight peptide compounds that have strong binding properties to the TPO-R, can activate the TPO-R and potentially permit reduced side effects compared to known TPO agonists. Accordingly, the peptide compounds can be useful for therapeutic purposes in treating conditions mediated by TPO (e.g., thrombocytopenia resulting from chemotherapy, radiation therapy, or bone marrow transfusions) as well as for diagnostic purposes in studying the mechanism of hematopoiesis and for the in vitro expansion of megakaroycytes and committed progenitor cells.

Peptide compounds suitable for therapeutic and/or diagnostic purposes have an $IC_{50}$ of about 2 mM or less, as determined by, for example, the binding affinity assay set forth in Example 3 of U.S. Pat. No. 5,869,451, wherein a lower $IC_{50}$ correlates to a stronger binding affinity to TPO-R. The assay in U.S. Pat. No. 5,869,451 is as follows: Binding affinities of peptide compounds are measured in a competition binding assay. The wells of a microtiter plate are coated with 1 mg streptavidin, blocked with PBS/1% BSA, followed by 50 ng of biotinylated anti-receptor immobilizing antibody (Ab179). The wells are then treated with a 1:10 dilution of soluble TPO-R harvest. Various concentrations of peptide compound are mixed with a constant amount of a truncated form of TPO consisting of residues 1-156 fused to the C-terminus of maltose binding protein (MBP-$TPO_{156}$). The peptide MBP-$TPO_{156}$ mixtures are added to the TPO-R coated wells, incubated for 2 hours at 4° C. and then washed with PBS. The amount of MBP-TPO that is bound at equilibrium is measured by adding a rabbit anti-sera directed against MBP, followed by alkaline phosphatase conjugated goat anti-rabbit IgG. The amount of alkaline phosphatase in each well is then determined using standard methods. The assay is conducted over a range of peptide compound concentrations and the results are graphed such that the y axis represents the amount of bound MBP-TPO and the x axis represents the concentration of peptide compound. One can then determine the concentration at which the peptide compound will reduce by 50% ($IC_{50}$) the amount of MBP-TPO bound to immobilized TPO-R. The dissociation constant (Kd) for the peptide should be similar to the measured $IC_{50}$ using these assay conditions. For pharmaceutical purposes, peptide compounds preferably have an $IC_{50}$ of no more than about 100 μM, more preferably, no more than 500 nM. In a preferred embodiment, the molecular weight of the peptide compound is from about 250 to about 8,000 daltons. If the peptide compound of this invention are oligomerized, dimerized and/or derivatized with a hydrophilic polymer as described herein, the molecular weights of such peptide compounds will be substantially greater and can range anywhere from about 500 to about 120,000 daltons, more preferable from about 8,000 to about 80,000 daltons.

When used for diagnostic purposes, the peptide compounds of the present invention preferably are labeled with a detectable label and, accordingly, the peptide compounds without such a label serve as intermediates in the preparation of labeled peptide compounds.

A peptide compound meeting the defined criteria for molecular weight and binding affinity for the TPO-R comprises 9 or more amino acids wherein the amino acids are naturally occurring or synthetic (non-naturally occurring) amino acids.

Accordingly, preferred peptide compounds comprise a compound having:

(1) a molecular weight of less than about 5000 daltons, and (2) a binding affinity to TPO-R as expressed by an $IC_{50}$ of no more than about 100 μM, wherein from zero to all of the —C(O)NH— linkages of the peptide compound have been replaced by a linkage selected from the group consisting of a —$CH_2OC(O)NR$— linkage; a phosphonate linkage; a—$CH_2S(O)_2NR$— linkage; a—$CH_2NR$— linkage; and a—$C(O)NR^6$— linkage; and a—$NHC(O)NH$— linkage where R is hydrogen or lower alkyl and $R^6$ is lower alkyl, further wherein the N-terminus of said peptide compound is selected from the group consisting of a —$NRR^1$ group; a—$NRC(O)R$ group; a—$NRC(O)OR$ group; a—$NRS(O)_2R$ group; a—$NHC(O)NHR$ group; a succinimide group; a benzyloxycarbonyl-NH— group; and a benzyloxycarbonyl-NH— group having from 1 to 3 substituents on the phenyl ring selected from the group consisting of lower alkyl, lower alkoxy, chloro, and bromo, where R and $R^1$ are independently selected from the group consisting of hydrogen and lower alkyl, and still further wherein the C-terminus of said peptide compound has the formula —$C(O)R^2$ where $R^2$ is selected from the group consisting of hydroxy, lower alkoxy, and —$NR^3R^4$ where $R^3$ and $R^4$ are independently selected from the group consisting of hydrogen and lower alkyl and where the nitrogen atom of the —$NR^3R^4$ group can optionally be the amine group of the N-terminus of the peptide so as to form a cyclic peptide, and physiologically acceptable salts thereof.

In a related embodiment, the invention is directed to a labeled peptide compound comprising a peptide compound described as above having covalently attached thereto a label capable of detection.

In one embodiment, the core peptide compound comprises a sequence of amino acids: (SEQ ID NO:2)

$X_9 X_8 G X_1 X_2 X_3 X_4 X_5 X_6 X_7$ where $X_9$ is A, C, E, G, I, L, M, P, R, Q, S, T, or V; and $X_8$ is A, C, D, E, K, L, Q, R, S, T, or V; and $X_6$ is a β-(2-naphthyl) alanine (referred to herein as "2-Nal") residue. More preferably, $X_9$ is A or I; and $X_8$ is D, E, or K. Further $X_1$ is C, L, M, P, Q, V; $X_2$ is F, K, L; N, Q, R, S, T or V; $X_3$ is C, F, I, L, M, R, S, V or W; $X_4$ is any of the 20 genetically coded L-amino acids; $X_5$ is A, D, E, G, K, M, Q, R, S, T, V or Y; and $X_7$ is C, G, I, K, L, M, N, R or V.

A particularly preferred peptide compound includes the amino acid sequence I E G P T L R Q (2-Nal) L A A R (Sar) (SEQ ID NO: 3), wherein (2-Nal) is β-(2-naphthyl)alanine and (Sar) is sarcosine.

In another embodiment, the peptide compounds of the present invention are preferably dimerized or oligomerized to increase the affinity and/or activity of the compounds. An example of a preferred dimerized peptide compound includes, but is not limited to, the following:

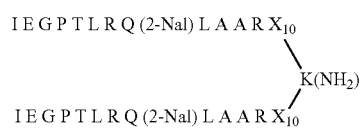

where $X_{10}$ is a sarcosine or β-alanine residue. The above structure can also be represented by the following structure: (H-IEGPTLRQ(2-Nal)LAAR$X_{10}$)$_2$K-$NH_2$.

When $X_{10}$ is a sarcosine, the compound has the following structure;

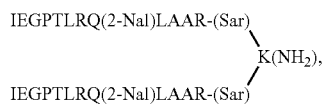

wherein (2-Nal) is β-(2-naphthyl)alanine and (Sar) is sarcosine. This peptide compound, which can also be represented by the following structure (H-IEGPTLRQ(2-Nal)LAAR(Sar))$_2$K-NH$_2$ is referred to herein as "TPO Compound No. 1".

In yet a further embodiment, preferred peptide compounds for use in this invention include peptide compounds that are covalently attached to one or more of a variety of hydrophilic polymers. Suitable hydrophilic polymers include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc., as described in U.S. Pat. No. 5,869,451, the entire content of which is hereby incorporated by reference.

The peptide compounds described herein are useful for the prevention and treatment of diseases mediated by TPO, and particularly for treating hematological disorders, including but not limited to, thrombocytopenia resulting from chemotherapy, radiation therapy, or bone marrow transfusions. Thus, the present invention also provides a method for treating wherein a patient having a disorder that is susceptible to treatment with a TPO agonist receives, or is administered, a therapeutically effective dose or amount of a peptide compound of the present invention.

The invention also provides for pharmaceutical compositions comprising one or more of the peptide compounds described herein and a physiologically acceptable carrier. These pharmaceutical compositions can be in a variety of forms including oral dosage forms, as well as inhalable powders and solutions and injectable and infusible solutions.

DESCRIPTION OF SPECIFIC EMBODIMENTS

I. Definitions and General Parameters

Figure 1:
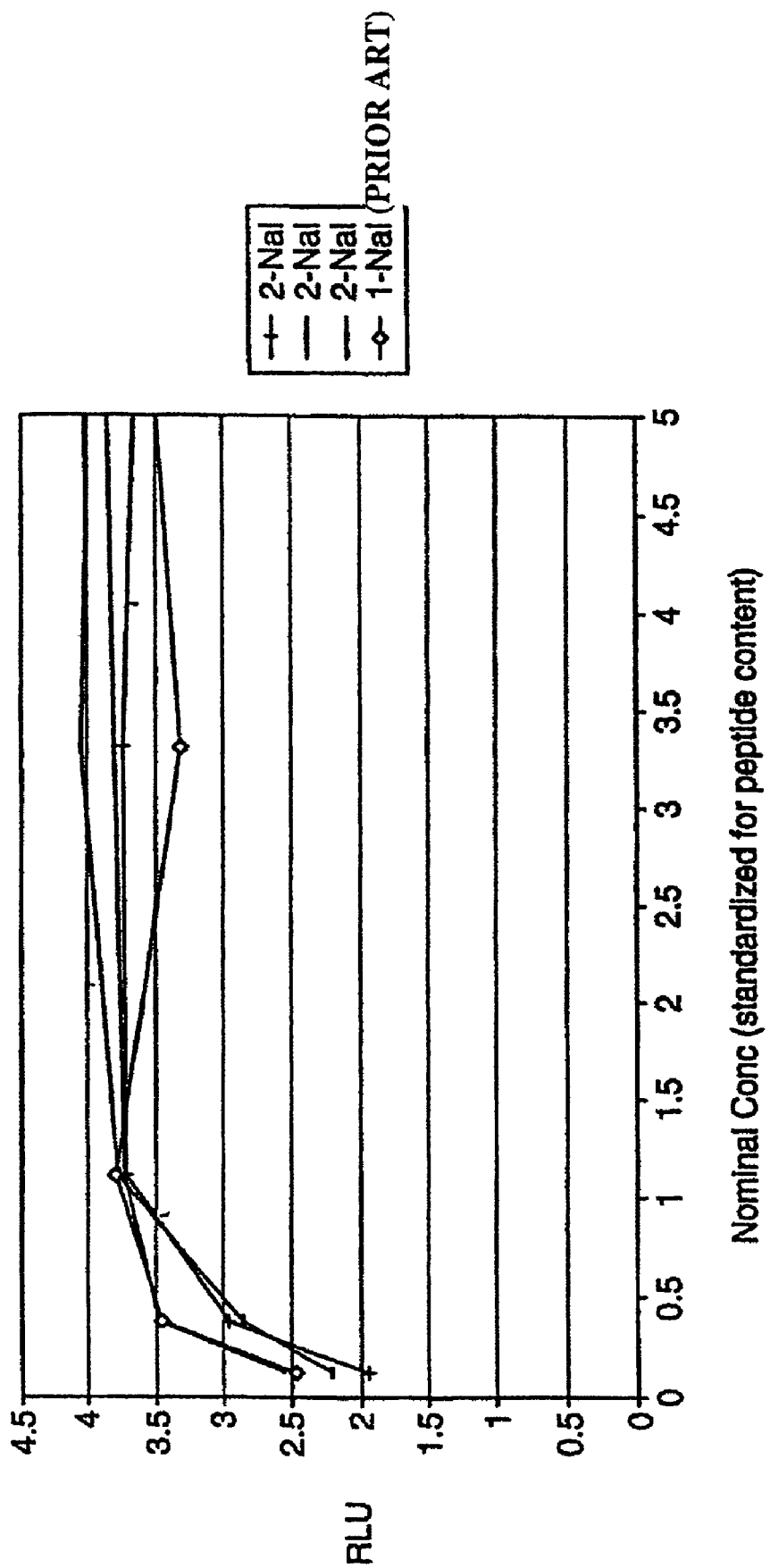
FIG. 1 shows and compares the activity of TPO Compound No. 1 to a prior art peptide compound (referred to throughout herein as "prior art peptide compound"). The difference between TPO Compound No 1 and the prior art peptide compound is that the prior art peptide compound has a β-(1-naphthyl)alanine (1-Nal) where (2-Nal) is on TPO Compound No. 1.

The following definitions are set forth to illustrate and define the meaning and scope of the various terms used to describe the invention herein.

"Agonist" refers to a biologically active ligand which binds to its complementary biologically active receptor and activates the latter either to cause a biological response in the receptor or to enhance preexisting biological activity of the receptor.

"Peptide compound" refers to a molecule that hydrolyzes into amino acids and/or amino acid derivatives and/or amino acid substitutes.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., supra.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., ed., Design of Prodrugs, Elsevier Science Publishers, Amsterdam (1985). These esters are, typically formed from the corresponding carboxylic acid and an alcohol. Generally, ester formation can be accomplished via conventional synthetic techniques. (See, e.g., March, Advanced Organic Chemistry, 4th Ed., John Wiley & Sons, New York (1992), 393-396 and references cited therein, and Mark, et al., Encyclopedia of Chemical Technology, John Wiley & Sons, New York (1980).) The alcohol component of the ester will generally comprise (i) a $C_2$-$C_{12}$ aliphatic alcohol that can or can not contain one or more double bonds and can or can not contain branched carbons or (ii) a $C_7$-$C_{12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., Design of Prodrugs, Elsevier Science Publishers, Amsterdam (1985). These amides are typically formed from the corresponding carboxylic acid and an amine. Generally, amide formation can be accomplished via conventional synthetic techniques. (See, e.g., March, Advanced Organic Chemistry, 4th Ed., John Wiley & Sons, New York (1992), p. 393 and Mark, et al. Encyclopedia of Chemical Technology, John Wiley & Sons, New York (1980).) This invention also contemplates the use of those compositions which are both amides as described herein and at the same time are the pharmaceutically acceptable acid addition salts thereof.

"Pharmaceutically or therapeutically acceptable carrier" refers to a carrier medium which does not interfere with the effectiveness of the biological activity of the active ingredients and which is not toxic to the host or patient.

"Stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds of the instant invention may have one or more asymmetrical carbon atoms and therefore include various stereoisomers. All stereoisomers are included within the scope of the invention.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve a decrease in the immunological and/or inflammatory responses to infection or tissue injury.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Additionally, t-Buo is tert-butyloxy, Bzl is benzyl, CHA is cyclohexylamine, Ac is acetyl, Me is methyl, Pen is penicillamine, Aib is aminoisobutyric acid, Nva is norvaline, Abu is aminobutyric acid, Thi is thienylalanine, OBn is O-benzyl, and hyp is hydroxyproline.

Peptide analogs are commonly used in the pharmaceutical industry as non-peptide drugs with properties analogous to those of the template peptide. These types of non-peptide compounds are termed "peptidemimetics" or "peptide mimetics" or "peptidomimetics" (Luthman, et al., A Textbook of Drug Design and Development, 14:386406, 2nd Ed., Harwood Academic Publishers (1996); Joachim Grante, Angew. Chem. Int. Ed. Engl., 33:1699-1720 (1994); Fauchere, J., Adv. Drug Res., 15:29 (1986); Veber and Freidinger TINS, p. 392 (1985); and Evans, et al., J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as naturally-occurring receptor-binding polypeptide, but have one or more peptide linkages optionally replaced by an alternative linkage such as —$CH_2NH$—, —$CH_2S$—, etc. by methods known in the art and further described in the following references: Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm. Sci. pp. 463-468 (1980), (general review); Hudson, et al., Int. J. Pept. Prot. Res., 14:177-185 (1979); Spatola, et al., Life Sci., 38:1243-1249 (1986); Hann, J. Chem. Soc. Perkin Trans. I, 307-314 (1982); Almquist, et al., J. Med. Chem., 23:1392-1398, (1980); Jennings-White, et al., Tetrahedron Lett. 23:2533 (1982); Szelke, et al., European Appln. EP 45665 (1982); Holladay, et al., Tetrahedron Lett., 24:4401-4404 (1983); and Hruby, Life Sci., 31:189-199 (1982); each of which is incorporated herein by reference. A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., immunoglobulin superfamily molecules) to which the peptidomimetic binds to produce the therapeutic effect. Derivitization (e.g., labeling) of peptidomimetics should not substantially interfere with the desired biological or pharmacological activity of the peptidomimetic. Generally, peptidomimetics of receptor-binding peptides bind to the receptor with high affinity and possess detectable biological activity (i.e., are agonistic or antagonistic to one or more receptor-mediated phenotypic changes).

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo, et al., Ann. Rev. Biochem., 61:387 (1992), incorporated herein by reference); for example, by adding internal cysteine residues capable of forming intramolecular disulfide bridges which cyclize the peptide.

"Detectable label" refers to materials, which when covalently attached to the peptide compounds of this invention, permit detection of the peptide compounds in vivo in the patient to whom the peptide compound has been administered. Suitable detectable labels are well known in the art and include, by way of example, radioisotopes, fluorescent labels (e.g., fluorescein), and the like. The particular detectable label employed is not critical and is selected relative to the amount of label to be employed as well as the toxicity of the label at the amount of label employed. Selection of the label relative to such factors is well within the skill of the art.

Covalent attachment of the detectable label to the peptide compound is accomplished by conventional methods well known in the art. For example, when the $^{125}I$ radioisotope is employed as the detectable label, covalent attachment of $^{125}I$ to the peptide compound can be achieved by incorporating the amino acid tyrosine into the peptide compound and then iodinating the peptide compound (see, e.g., Weaner, et al., Synthesis and Applications of Isotopically Labelled Compounds, pp. 137-140 (1994)). Incorporation of tyrosine to the N or C terminus of the peptide compound can be achieved by well known chemistry. Likewise, $^{32}P$ can be incorporated onto the peptide compound as a phosphate moiety through, for example, a hydroxyl group on the peptide compound using conventional chemistry.

II. Overview

The present invention provides peptide compounds that bind to and activate the TPO-R or otherwise behave as a TPO agonist. These peptide compounds include "lead" peptide compounds and "derivative" peptide compounds constructed so as to have the same or similar molecular structure or shape as the lead peptide compounds but that differ from the lead peptide compounds either with respect to susceptibility to hydrolysis or proteolysis and/or with respect to other biological properties, such as increased affinity for the receptor. The present invention also provides compositions comprising an effective amount of a peptide compound, and more particularly a peptide compound, that is useful for treating hematological disorders, and particularly, thrombocytopenia associated with chemotherapy, radiation therapy, or bone marrow transfusions.

It was found that the core peptide compound can comprises a sequence of amino acids: (SEQ ID NO:2): $X_9 X_8 G X_1 X_2 X_3 X_4 X_5 X_6 X_7$, where $X_6$ may be β-(2-naphthyl)alanine and where $X_9$ is A, C, E, G, I, L, M, P, R, Q, S, T, or V; and $X_8$ is A, C, D, E, K, L, Q, R, S, T, or V. More preferably, $X_9$ is A or I; and $X_8$ is D, E, or K. Further $X_4$ is C, L, M, P, Q, V; $X_2$ is F, K, L, N, Q, R, S, T or V; $X_3$ is C, F, I, L, M, R, S, V or W; $X_4$ is any of the 20 genetically coded L-amino acids; $X_5$ is A, D, E, G, K, M, Q, R, S, T, V or Y; and $X_7$ is C, G, I, K, L, M, N, R or V.

However, as described further herein, it has been found that by replacing $X_6$ with β-(2-naphthyl)alanine, the compound provides different properties over the compound containing β-(1-naphthyl)alanine. Accordingly, a particularly preferred peptide compound includes the amino acid sequence (SEQ ID NO: 3): I E G P T L R Q (2-Nal) L A A R (Sar).

In another embodiment, the peptide compounds of the present invention are preferably dimerized or oligomerized to increase the affinity and/or activity of the compounds. An example of a preferred dimerized peptide compound includes, but is not limited to, the following:

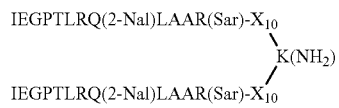

where $X_{10}$ is a sarcosine or β-alanine residue. It should be noted that one $X_{10}$ residue can be sarcosine and the other residue can be β-alanine. The above structure can also be represented by the following: (H-IEGPTLRQ(2-Nal) LAARX$_{10}$)$_2$K-NH$_2$.

A preferred peptide compound is as follows:

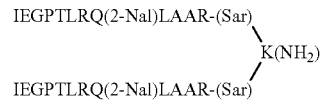

wherein (2-Nal) is β-(2-naphthyl)alanine and (Sar) is sarcosine. This peptide compound is referred to herein as "TPO Compound No. 1".

Peptide compounds having an $IC_{50}$ of greater than about 100 mM lack sufficient binding to permit use in either the diagnostic or therapeutic aspects of this invention. Preferably, for diagnostic purposes, the peptide compounds have an $IC_{50}$ of about 2 mM or less and, for pharmaceutical purposes, the peptide compounds have an $IC_{50}$ of about 100 µM or less.

FIG. 1 compares the activity of three different batches of TPO Compound No. 1 with one batch of prior art peptide compound using standard relative luminescent units assay techniques. The assay employs murine cells engineered to stably express the human TPO receptor and a luciferase reporter construct driven by the fos promoter. The difference between TPO Compound No. 1 and the prior art peptide compound is that the prior art peptide compound has a β-(1-naphthyl)alanine (1-Nal) where the (2-Nal) is on TPO Compound No. 1. TPO Compound No. 1 is referred to as 2-Nal and the prior art peptide compound is referred to as 1-Nal (Prior Art) in FIG. 1. As shown from FIG. 1, the activity is similar for each compound.

Figure 2:
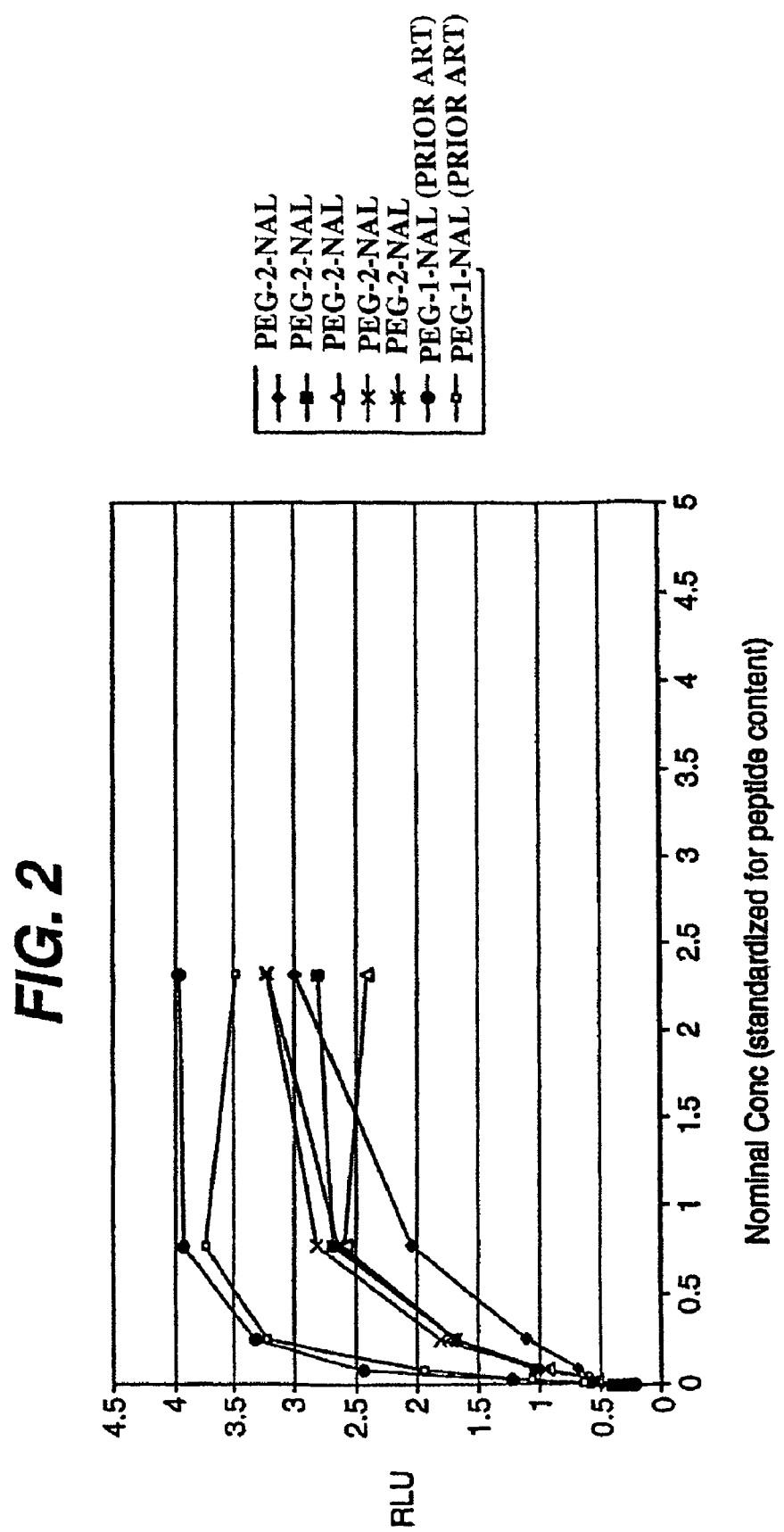
FIG. 2 shows and compares the activity of PEGylated TPO Compound No. 1 to PEGylated prior art peptide compound.

FIG. 2 compares the activity of several different batches of PEGylated TPO Compound No. 1 (pegylation of the compounds of the present invention is described in more detail below). Both batches of the PEGylated prior art peptide compound show high activity with essentially the same level of activity as the un-PEGylated prior art peptide compound. The remaining lines illustrate the activity of different batches of PEGylated TPO Compound No. 1. As shown by FIG. 2, in this model, the latter have less activity relative to the PEGylated prior art peptide compounds, PEGylated TPO Compound No. 1 is referred to as PEG-2-Nal and PEGylated prior art peptide compound is referred to as PEG-1-Nal (Prior Art) in FIG. 2.

Figure 3:
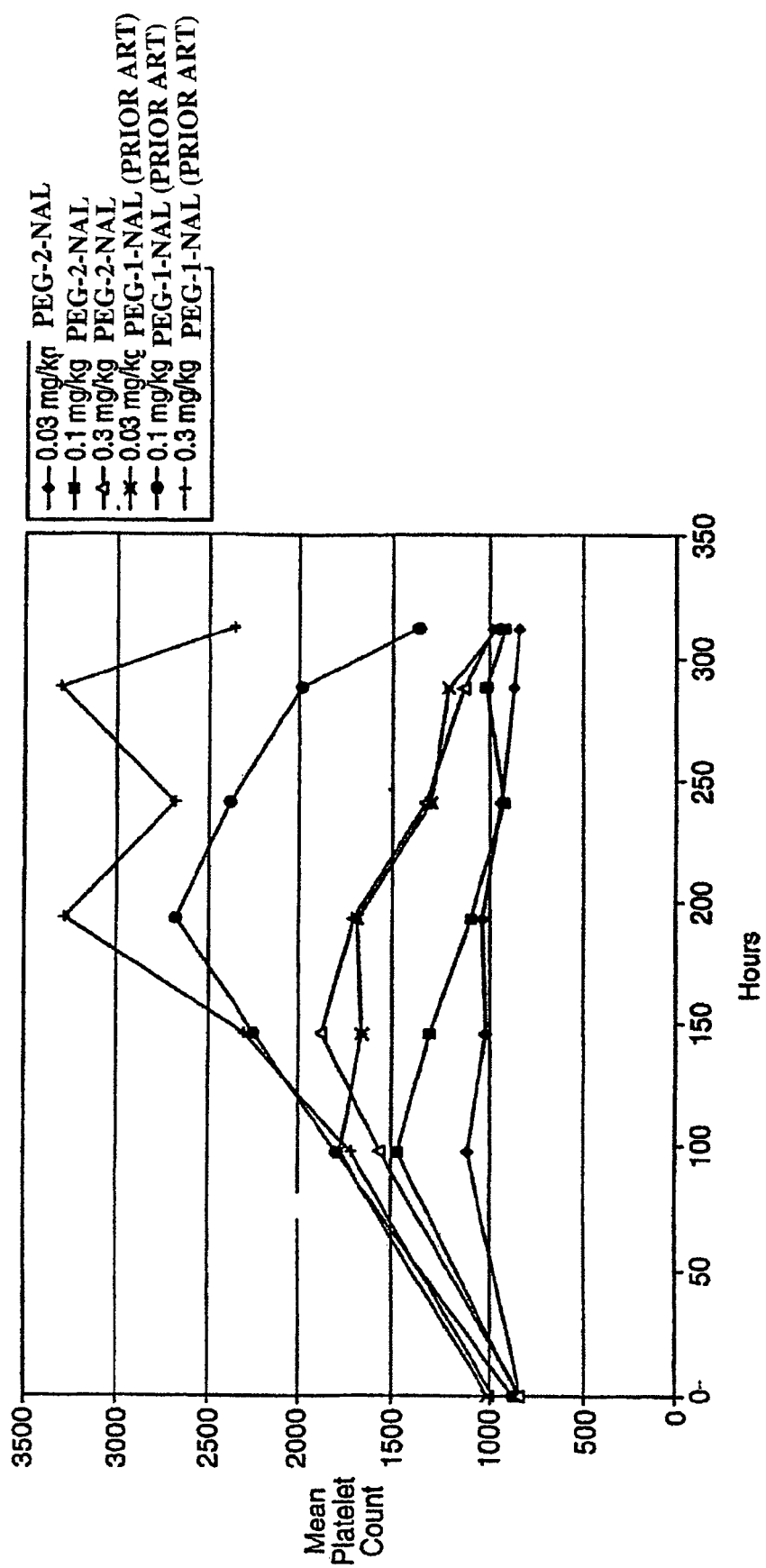
FIG. 3 shows and compares the in vivo change in platelet counts in rat demonstrating the relative potency of PEGylated TPO Compound No. 1 to PEGylated prior art peptide compound.

FIG. 3 demonstrates the relative potency of PEGylated prior art peptide compound and PEGylated TPO Compound No. 1. Through a rat model, FIG. 3 shows the in-vivo change in platelet counts after administration of PEGylated prior art peptide compound and PEGylated TPO Compound No. 1. As shown by FIG. 3, the highest dose of the PEGylated TPO Compound No. 1 has the same activity as the lowest dose of the PEGylated prior art peptide compound. A less potent compound may provide a less drastic stimulus to the target cell, which could reduce the risk of side effects caused by overstimulation of the target cell, such as exacerbated thrombocytopenia following subsequent cycle of chemotherapy. PEGylated TPO Compound No. 1 is referred to as PEG-2-Nal and PEGylated prior art peptide compound is referred to as PEG-1-Nal (Prior Art) in FIG. 3.

Figure 4:
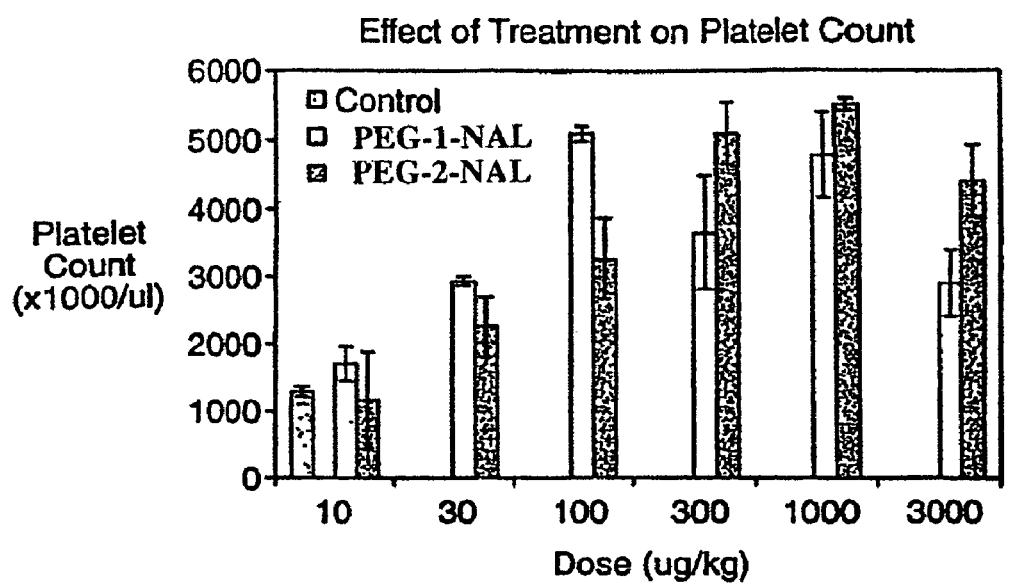
FIGS. 4 and 5 show and compare the number and volume of circulating platelets in a dose dependent manner, respectively upon the use of PEGylated prior art peptide compound and the use of PEGylated TPO Compound No. 1.
Figure 5:
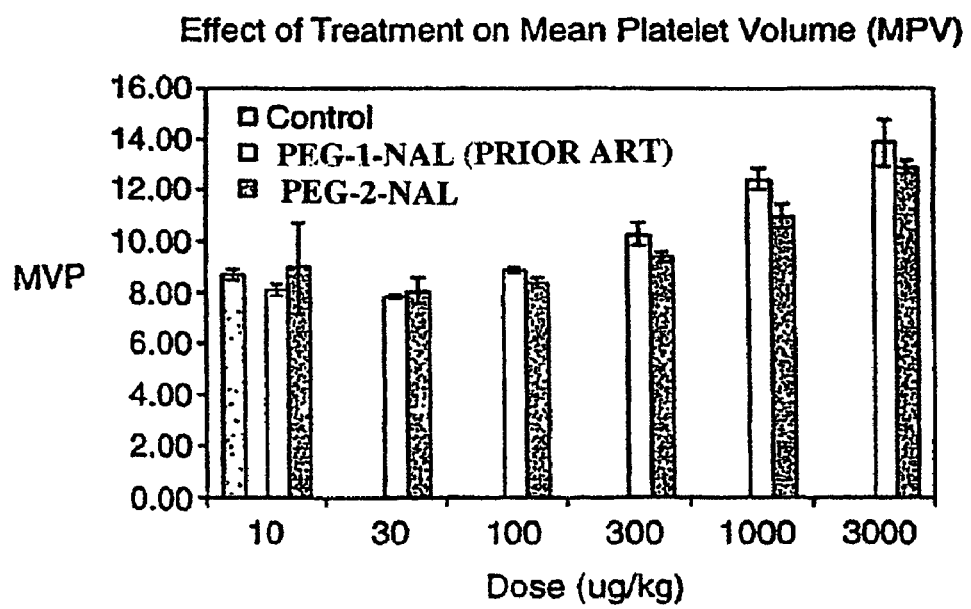

FIGS. 4 and 5 show the results of a head-to-head dose response study of a PEGylated prior art peptide compound and PEGylated TPO Compound No. 1 in normal mice. PEGylated TPO Compound No. 1 is referred to as PEG-2-Nal and PEGylated prior art peptide compound is referred to as PEG-1-Nal (Prior Art) in FIGS. 4 and 5. FIG. 4 shows increases in platelet levels and FIG. 5 shows Mean Platelet Volume six (6) days following treatment. The dose range was from 10 to 3000 ug/kg. Both peptide compounds increased the number of circulating platelets in a dose-dependent manner with increases relative to the control group observed at doses as low as 30 ug/kg for both compounds. At the maximal response, these peptide compounds elevated platelet counts to levels that were up to 4-fold greater than control values. The dose-response curves for these peptide compounds were very similar indicating that in this model there was essentially no difference between the two test articles based on these endpoints.

IV. Preparation of Peptide Compounds

A. Solid Phase Synthesis

The peptide compounds of the invention can be prepared by classical methods known in the art, for example, by using standard solid phase techniques. The standard methods include exclusive solid phase synthesis, partial solid phase synthesis methods, fragment condensation, classical solution synthesis, and even by recombinant DNA technology. See, e.g., Merrifield, J. Am. Chem. Soc., 85:2149 (1963), incorporated herein by reference. On solid phase, the synthesis is typically commenced from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky, et al., Chem. Ind. (London), 38:1597 (1966). The benzhydrylamine (BHA) resin has been described by Pietta and Marshall, Chem. Commn., 650 (1970) and is commercially available from Beckman Instruments, Inc., Palo Alto, Calif., in the hydrochloride form.

Thus, the peptide compounds of the invention can be prepared by coupling an alpha-amino protected amino acid to the chloromethylated resin with the aid of, for example, cesium bicarbonate catalyst, according to the method described by Gisin, Helv. Chim. Acta., 56:1467 (1973). After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g. benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z—Br—Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting group for Thr and Ser is benzyl. The side chain protecting groups for Arg include nitro, Tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl—Cbz), 2-bromobenzyloxycarbonyl (2-BrCbz), Tos, or Boc.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by John Morrow Stewart and Janis Dillaha Young, Solid Phase Peptide Syntheses (2nd Ed., Pierce Chemical Company, 1984).

B. Synthetic Amino Acids

These procedures can also be used to synthesize peptides in which amino acids other than the 20 naturally occurring, genetically encoded amino acids are substituted at one, two, or more positions of any of the compounds of the invention.

One can replace the naturally occurring side chains of the 20 genetically encoded amino acids (or D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify the peptides of the instant invention by phosphorylation (see, e.g., W. Bannwarth, et al., Biorganic and Medicinal Chemistry Letters, 6(17):2141-2146 (1996)), and other methods for making peptide derivatives of the compounds of the present invention are described in Hruby, et al., Biochem. J., 268(2):249-262 (1990). Thus, the peptide compounds of the invention also serve as a basis to prepare peptide mimetics with similar biological activity.

C. Terminal Modifications

Those of skill in the art recognize that a variety of techniques are available for constructing peptide compounds with the same or similar desired biological activity as the corresponding peptide compound but with more favorable activity than the peptide compound with respect to solubility, stability, and susceptibility to hydrolysis and proteolysis. See, for example, Morgan, et al., Ann. Rep. Med. Chem., 24:243-252 (1989). The following describes methods for preparing peptide compounds modified at the N-terminal amino group, the C-terminal carboxyl group, and/or changing one or more of the amido linkages in the peptide to a non-amido linkage. It being understood that two or more such modifications can be coupled in one peptide compound structure (e.g., modification at the C-terminal carboxyl group and inclusion of a —CH$_2$-carbamate linkage between two amino acids in the peptide compound).

1. N-Terminal Modifications

The peptide compounds typically are synthesized as the free acid but, as noted above, could be readily prepared as the amide or ester. One can also modify the amino and/or carboxy terminus of the peptide compounds of the invention to produce other compounds of the invention. Amino terminus modifications include methylation, acetylation, adding a benzyloxycarbonyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints.

Amino terminus modifications are as recited above and include alkylating, acetylating, adding a carbobenzoyl group, forming a succinimide group, etc. (See, e.g., Murray, et al., Burger's Medicinal Chemistry and Drug Discovery, 5th ed., Vol. 1, Manfred E. Wolf, ed., John Wiley and Sons, Inc. (1995).) Specifically, the N-terminal amino group can then be reacted as follows:

(a) to form an amide group of the formula RC(O)NH— where R is as defined above by reaction with an acid halide or symmetric anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—;

(b) to form a succinimide group by reaction with succinic anhydride. As before, an approximately equimolar amount or an excess of succinic anhydride (e.g., about 5 equivalents) can be employed and the amino group is converted to the succinimide by methods well known in the art including the use of an excess (e.g., ten equivalents) of a tertiary amine such as diisopropylethylamine in a suitable inert solvent (e.g., dichloromethane). See, for example, Wollenberg, et al., U.S. Pat. No. 4,612,132 which is incorporated herein by reference in its entirety. It is understood that the succinic group can be substituted with, for example, alkyl or —SR substituents which are prepared in a conventional manner to provide for substituted succinimide at the N-terminus of the peptide. Such alkyl substituents are prepared by reaction of a lower olefin with maleic anhydride in the manner described by Wollenberg, et al., supra and —SR substituents are prepared by reaction of RSH with maleic anhydride where R is as defined above;

(c) to form a benzyloxycarbonyl-NH— or a substituted benzyloxycarbonyl-NH— group by reaction with approximately an equivalent amount or an excess of CBZ—Cl (i.e., benzyloxycarbonyl chloride) or a substituted CBZ—CL in a suitable inert diluent (e.g., dichloromethane) preferably containing a tertiary amine to scavenge the acid generated during the reaction;

(d) to form a sulfonamide group by reaction with an equivalent amount or an excess (e.g., 5 equivalents) of R—S(O)$_2$ Cl in a suitable inert diluent (dichloromethane) to convert the terminal amine into a sulfonamide where R is as defined above. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes);

(e) to form a carbamate group by reaction with an equivalent amount or an excess (e.g., 5 equivalents) of R—OC(O)Cl or R—OC(O)OC$_6$H$_4$-p-NO$_2$ in a suitable inert diluent (e.g., dichloromethane) to convert the terminal amine into a carbamate where R is as defined above. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes); and (f) to form a urea group by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. Preferably, the inert diluent contains an excess (e.g., about 10 equivalents) of a tertiary amine, such as diisopropylethylamine. Reaction conditions are otherwise conventional (e.g., room temperature for about 30 minutes).

2. C-Terminal Modifications

In preparing peptide compounds wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

In preparing peptide compounds wherein the C-terminal carboxyl group is replaced by the amide —C(O)NR$^3$ R$^4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide (i.e., the C-terminus is —C(O)NRR$^1$ where R and R$^1$ are as defined above). Side chain protection is then removed in the usual fashion by treatment with hydrogen fluoride to give the free amides, alkylamides, or dialkylamides.

One can also cyclize the peptide compounds of the invention, or incorporate a desamino or descarboxy residue at the terminii of the peptide compound, so that there is no terminal amino or carboxyl group, to decrease susceptibility to proteases or to restrict the conformation of the peptide compound. C-terminal functional groups of the peptide compounds of the present invention include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, the peptide compounds of the invention, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. The foregoing can be accomplished with little, if any, diminishment in their binding activity. Nonproteinaceous polymers suitable for use in accordance with the present invention include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have an average molecular weight of about 5,000 daltons, 10,000 daltons and 20,000 daltons.

The peptide compounds of the invention can be derivatized with or coupled to such polymers using any of the methods set forth in Zallipsky, S., Bioconjugate Chem., 6:150-165 (1995); Monfardini, C, et al., Bioconjugate Chem., 6:62-69 (1995); U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 or WO 95/34326, all of which are incorporated by reference in their entirety herein.

In a presently preferred embodiment, the peptide compounds of the present invention are derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a presently preferred embodiment, the PEGs employed have molecular weights ranging from 5,000 daltons to about 20,000 daltons. PEGs coupled to the peptide compounds of the present invention can be either branched or unbranched. (See, e.g., Monfardini, C., et al., Bioconjugate Chem., 6:62-69 (1995)). PEGs are commercially available from Shearwater Polymers, Inc. (Huntsville, Ala.) (now part of Nektar Therapeutics (San Carlo, Calif.), Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM).

Briefly, in one embodiment, the hydrophilic polymer which is employed, e.g., PEG, is preferably capped at one end by an unreactive group such as a methoxy or ethoxy group. Thereafter, the polymer is activated at the other end by reaction with a suitable activating agent, such as cyanuric halides (e.g., cyanuric chloride, bromide or fluoride), diimadozle, an anhydride reagent (e.g., a dihalosuccinic anhydride, such as dibromosuccinic anhydride), acyl azide, p-diazoiumbenzyl ether, 3-(p-diazoniumphenoxy)-2-hydroxypropylether) and the like. The activated polymer is then reacted with a peptide compound of the present invention to produce a peptide compound derivatized with a polymer. Alternatively, a functional group in the peptide compounds of the invention can be activated for reaction with the polymer, or the two groups can be joined in a concerted coupling reaction using known coupling methods. It will be readily appreciated that the peptide compounds of the invention can be derivatized with PEG using a myriad of other reaction schemes known to and used by those of skill in the art.

When the peptide compounds are derivatized with a hydrophillic polymer, their solubility and circulation half-lives are increased and their immunogenicity is decreased. The foregoing can be accomplished with little, if any, loss in biological activity. In preferred embodiments, the derivatized peptides have an activity that is 0.1 to 0.01-fold that of the unmodified peptides. In more preferred embodiments, the derivatized peptides have an activity that is 0.1 to 1-fold that of the unmodified peptides. In even more preferred embodiments, the derivatized peptides have an activity that is greater than the unmodified peptides.

D. Backbone Modifications

Other methods for making peptide derivatives of the compounds of the present invention are described in Hruby, et al., Biochem J., 268(2):249-262 (1990), incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan, et al., Ann. Rep. Med. Chem., 24:243-252 (1989), incorporated herein by reference. These techniques include replacing the peptide backbone with a backbone composed of phosphonates, amidates, carbamates, sulfonamides, secondary amines, and N-methylamino acids.

Suitable reagents include, for example, amino acid analogues wherein the carboxyl group of the amino acid has been replaced with a moiety suitable for forming one of the above linkages.

Similarly, replacement of an amido linkage in the peptide with a phosphonate linkage can be achieved in the manner set forth in U.S. Pat. Nos. 5,359,115 and 5,420,328, the disclosures of which are incorporated herein by reference in their entirety.

E. Disulfide Bond Formation

The compounds of the present invention may exist in a cyclized form with an intramolecular disulfide bond between the thiol groups of incorporated cysteines, if present. Alternatively, an intermolecular disulfide bond between the thiol groups of the cysteines can be produced to yield a dimeric (or higher oligomeric) compound. One or more of the cysteine residues may also be substituted with a homocysteine.

V. Utility

The peptide compounds of the invention are useful in vitro as unique tools for understanding the biological role of TPO, including the evaluation of the many factors thought to influence, and be influenced by, the production of TPO and the receptor binding process. The present peptide compounds are also useful in the development of other compounds that bind to and activate the TPO-R, because the present peptide compounds provide important information on the relationship between structure and activity that should facilitate such development.

The peptide compounds are also useful as competitive binders in assays to screen for new TPO receptor agonists. In such assay embodiments, the peptide compounds of the invention can be used without modification or can be modified in a variety of ways; for example, by labeling, such as covalently or non-covalently joining a moiety which directly or indirectly provides a detectable signal. In any of these assays, the materials thereto can be labeled either directly or indirectly. Possibilities for direct labeling include label groups such as: radiolabels such as 125 I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups. The peptide compounds may also include spacers or linkers in cases where the peptide compounds are to be attached to a solid support.

Moreover, based on their ability to bind to the TPO receptor, the peptide compounds of the present invention can be used as reagents for detecting TPO receptors on living cells, fixed cells, in biological fluids, in tissue homogenates, in purified, natural biological materials, etc. For example, by labelling such peptide compounds, one can identify cells having TPO-R on their surfaces. In addition, based on their ability to bind the TPO receptor, the peptide compounds of the present invention can be used in in situ staining, FACS (fluorescence-activated cell sorting), Western blotting, ELISA, etc. In addition, based on their ability to bind to the TPO receptor, the peptide compounds of the present invention can be used in receptor purification, or in purifying cells expressing TPO receptors on the cell surface (or inside permeabilized cells).

The peptide compounds of the present invention can also be utilized as commercial reagents for various medical research and diagnostic uses. Such uses include but are not limited to: (1) use as a calibration standard for quantitating the activities of candidate TPO agonists in a variety of functional assays; (2) use to maintain the proliferation and growth of TPO-dependent cell lines; (3) use in structural analysis of the TPO-receptor through co-crystallization; (4) use to investigate the mechanism of TPO signal transduction/receptor activation; and (5) other research and diagnostic applications wherein the TPO-receptor is preferably activated or such activation is conveniently calibrated against a known quantity of a TPO agonist, and the like.

The peptide compounds of the present invention can be used for the in vitro expansion of megakaryocytes and their committed progenitors, both in conjunction with additional cytokines or on their own. See, e.g., DiGiusto, et al., PCT Publication No. 95/05843, which is incorporated herein by reference. Chemotherapy and radiation therapies cause thrombocytopenia by killing the rapidly dividing, more mature population of megakaryocytes. However, these therapeutic treatments can also reduce the number and viability of the immature, less mitotically active megakaryocyte precursor cells. Thus, amelioration of the thrombocytopenia by TPO or the compounds of the present invention can be hastened by infusing patients post chemotherapy or radiation therapy with a population of his or her own cells enriched for megakaryocytes and immature precursors by in vitro culture.

The peptide compounds of the invention can also be administered to warm blooded animals, including humans, to activate the TPO-R in vivo. Thus, the present invention encompasses methods for therapeutic treatment of TPO related disorders that comprise administering a peptide compound of the invention in amounts sufficient to mimic the effect of TPO on TPO-R in vivo. For example, the peptide compounds of the invention can be administered to treat a variety of hematological disorders, including but not limited to platelet disorders and thrombocytopenia, particularly when associated with bone marrow transfusions, radiation therapy, and chemotherapy.

In some embodiments of the invention, TPO antagonists are preferably first administered to patients undergoing chemotherapy or radiation therapy, followed by administration of the TPO agonists of the invention.

The activity of the peptide compounds of the present invention can be evaluated either in vitro or in vivo in one of the numerous models described in McDonald, Am. J. of Pediatric Hematology/Oncology, 14:8-21 (1992), which is incorporated herein by reference.

According to one embodiment, the compositions of the present invention are useful for treating thrombocytopenia associated with bone marrow transfusions, radiation therapy, or chemotherapy. The peptide compounds typically will be administered prophylactically prior to chemotherapy, radiation therapy, or bone marrow transplant or after such exposure.

Accordingly, the present invention also provides pharmaceutical compositions comprising, as an active ingredient, at least one of the peptide compounds of the invention in association with a pharmaceutical carrier or diluent. The peptide compounds of this invention can be administered by oral, pulmonary, parental (intramuscular, intraperitoneal, intravenous (IV) or subcutaneous injection), inhalation (via a fine powder formulation), transdermal, nasal, vaginal, rectal, or sublingual routes of administration and can be formulated in dosage forms appropriate for each route of administration. See, e.g., Bernstein, et al., PCT Patent Publication No. WO 93/25221; Pitt, et al., PCT Patent Publication No. WO 94/17784; and Pitt, et al., European Patent Application 613, 683, each of which is incorporated herein by reference.

Solid dosage forms for oral administration include capsules, tablets, pills, powders, and granules. In such solid dosage forms, the active peptide compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parental administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The compositions containing the peptide compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective dose". Amounts effective for this use will depend on the severity of the disease and the weight and general state of the patient.

The compositions of the invention can also be microencapsulated by, for example, the method of Tice and Bibi (in Treatise on Controlled Drug Delivery, ed. A. Kydonieus, Marcel Dekker, New York (1992), pp. 315-339).

In prophylactic applications, compositions containing the peptide compounds of the invention are administered to a patient susceptible to or otherwise at risk of a particular disease. Such an amount is defined to be a "prophylactically effective dose". In this use, the precise amounts again depend on the patient's state of health and weight.

The quantities of the peptide compound necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds), Goodman and Gilman's: The Pharmacological Basis of Therapeutics, 8th ed., Pergamon Press (1990); and Remington's Pharmaceutical Sciences, 7th Ed., Mack Publishing Co., Easton, Pa. (1985); each of which is hereby incorporated by reference.

The peptide compounds of this invention are effective in treating TPO mediated conditions when administered at a dosage range of from about 0.001 mg to about 10 mg/kg of body weight per day. The specific dose employed is regulated by the particular condition being treated, the route of administration as well as by the judgement of the attending clinician depending upon factors such as the severity of the condition, the age and general condition of the patient, and the like.

EXAMPLE 1

Solid Phase Peptide Compound Synthesis

The peptide compounds of the invention can be synthesized, for example, using the Merrifield solid phase synthesis techniques (see Steward and Young, Solid Phase Peptide Synthesis, 2d. edition, Pierce Chemical, Rockford, Ill. (1984) and Merrifield, J. Am. Chem. Soc., 85:2149 (1963)) or an Applied Biosystems Inc. Model 431A or 433A peptide synthesizer. The peptide compounds can be assembled using standard protocols of the Applied Biosystems Inc. SynthAssist™ 1.0.0 or Synth Assist™ 2.0.2. Each coupling can be performed for 2×30 min. with HBTU (2-(1H-benzatriazol-1-yl)-1,1,3,3-tetramethyluronium hexafluorophosphate) and HOBt (1-hydroxybenzotriazole).

The resin used can be HMP resin (p-hydroxymethyl phenoxymethyl)polystyrene resin or PAL (Milligen/Biosearch), which is a cross-linked polystyrene resin with 5-(4'-Fmoc-aminomethyl-3,5'-dimethyoxyphenoxy)valeric acid as a linker. Use of PAL resin results in a carboxyl terminal amide functionality upon cleavage of the peptide from the resin. Upon cleavage, the HMP resin produces a carboxylic acid moiety at the C-terminus of the final product. Most reagents, resins, and protected amino acids (free or on the resin) can be purchased from Millipore or Applied Biosystems Inc.

The Fmoc group can be used for amino protection during the coupling procedure. Primary amine protection on amino acids can be achieved with Fmoc and side chain protection groups such as t-butyl for serine, tyrosine, glutamic acid, and threonine; trityl for glutamine; Pmc (2,2,5,7,8-pentamethyl-chroman-6-sulfonyl) for arginine; N-t-butyloxycarbonyl for tryptophan; N-trityl for histidine and S-trityl for cysteine can be employed.

Removal of the peptide compounds from the resin and simultaneous deprotection of the side chain functions can be achieved by treatment with reagent K or slight modifications of it. Alternatively, in the synthesis of those peptides, with an amidated carboxyl terminus, the fully assembled peptide can be cleaved with a mixture of 90% trifluoroacetic acid, 5% ethanedithiol, and 5% water, initially at 4° C., and gradually increasing to room temperature. The deprotected peptide compounds can be precipitated with diethyl ether. Purification can be by preparative, reverse-phase, high performance liquid chromatography on a $C_{18}$ bonded silica gel column with a gradient of acetonitrile/water in 0.1% trifluoroacetic acid. The homogeneous peptide compounds can be characterized by Fast Atom Bombardment mass spectrometry or electrospray mass spectrometry and amino acid analysis when applicable.

In a preferred embodiment, the peptide compounds of this invention are dimerized using standard synthetic procedures known to and used by those of skill in the art. Following these synthetic schemes, those of skill in the art can readily prepare dimer peptide compounds in accordance with the present invention. In addition, it will be readily apparent to those of skill in the art that the dimeric subunits can readily be linked using known methodologies and linkers.

EXAMPLE 2

Pegylation of the Peptide Compounds

Pegylation of a peptide compound of the present invention can be carried out by well-known techniques. For example, a peptide compound of the invention can be dissolved in 100 mM bicine pH 8.0 at a concentration of 10 mg/ml, added to a 1.25 fold molar excess of powdered PEG2 (commercially available from Shearwater Polymers, Inc. (Huntsville, Ala., now Nektar Therapeutics (San Carlo, Calif.)) and stirred at room temperature until the reaction is complete, typically 1-2 hours. The reaction is monitored by reverse phase HPLC using a 40-65% acetonitrile gradient with a YMC ODS AQ column. When the reaction is complete, the solution is added to a second 1.25 molar excess of powdered PEG2 and the process is repeated 4 times using a total of 5 moles of PEG2 for each mole of polypeptide. The solution is diluted 2 fold with PBS to reduce the viscosity and loaded onto a superdex 200 column (Pharmacia), previously equilibrated and eluted with PBS. Fractions from the size exclusion column can be analyzed by reverse phase HPLC. Fractions containing di-PEG-polypeptide which elutes prior to any mono-PEG peptide compound can be pooled and stored at 5° C. or lyophilized.

EXAMPLE 3

Pre-Clinical Animal Studies on the Thrombopoietic Activity of TPO PEGylated Compound No. 1

TPO Compound No. 1 does not share any sequence homology with endogenous TPO, mitigating the risk of the formation of antibodies cross-reacting with endogenous TPO. TPO Compound No. 1 was PEGylated to reduce clearance and to further reduce antigenicity. This Example describes pre-clinical studies on the thrombopoietic activity of PEGylated TPO Compound No. 1 in an animal.

Normal male Wistar rats (source) were used for the studies. Other animals, such as dogs, mice, monkeys, etc. can also be used for the pre-clinical studies. All procedures involving animals were conducted in an animal facility fully accredited by the American Association for Assessment and Accreditation of Laboratory Animal Care (AAALAC) and in accordance with The Guide for the Care and Use of Laboratory Animals (NIH).

Normal male Wistar rats (10 weeks of age, 230 to 367 grams body weight range at dosing) were treated with single intravenous doses of TPO Compound No. 1 at 30, 100 or 300 ug/kg (40 rats/group). At predose, 96, 144, 192, 240, 288 and 312 hours post dose, approximately 0.5 mL of blood was collected by puncture of the jugular vein of unanesthetized rats (5 rats per time point, EDTA as anticoagulant) and platelet counts were assessed using a automated hematology analysis system. Animals were fasted overnight, with water available, prior to each sample collection.

Figure 6:
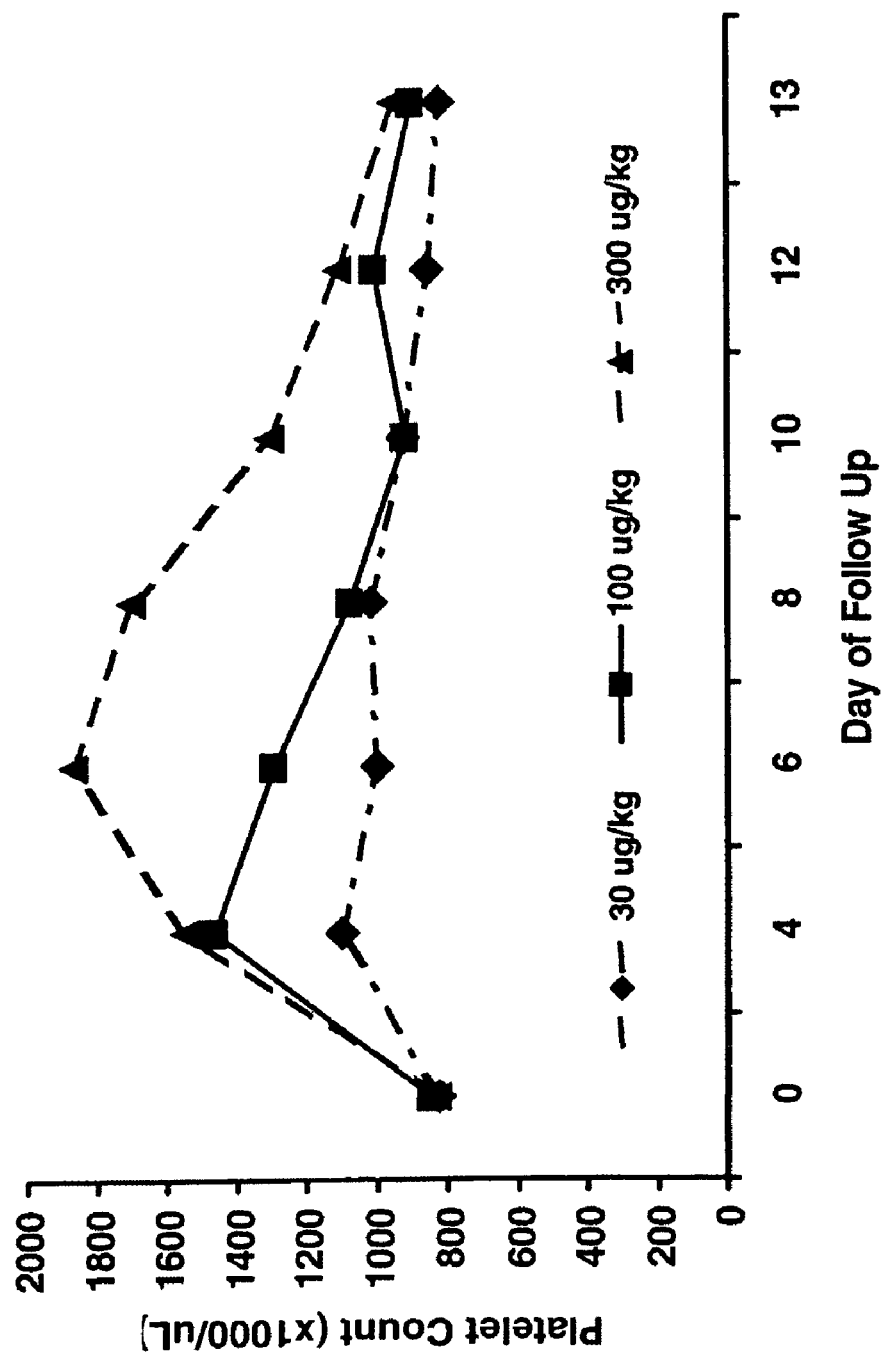
FIG. 6 shows that single intravenous doses of PEGylated TPO Compound No. 1 (30, 100 or 300 μg/kg) result in an increased peripheral platelet count in normal male Wistar rats.

Single intravenous doses of PEGylated TPO Compound No. 1 (30, 100 or 300 µg/kg) resulted in an increased peripheral platelet count in normal male Wistar rats by the earliest post-dose assessment on Day 4 (FIG. 6). Platelet counts were assessed every 2 days during the 2-week follow-up and compared with the predose count. The 300 µg/kg dose induced the greatest increase in platelet count, which returned to baseline by Day 14.

EXAMPLE 4

Phase I Clinical Studies on the Thrombopoietic Activity of PEGylated TPO Compound No. 1

Phase I studies were conducted to investigate the tolerability, pharmacodynamics and pharmacokinetics of PEGylated TPO Compound No. 1. This example describes Phase I studies on PEGylated TPO Compound No. 1 after a single intravenous injection in healthy male volunteers. Phase I studies on PEGylated TPO Compound No. 1 and other compounds according to the invention after multiple intravenous injection or other means of administration and/or to a patient in need of a treatment can be performed using protocols known to a person skilled in the art.

Forty volunteers were randomized to receive PEGylated TPO Compound No. 1 or placebo as a single i.v. bolus injection in a ratio of 6:2. Eight subjects were randomized in 6:2 ratio to receive a single injection of PEGylated TPO Compound No. 1 or placebo, with a dose range of 0.375, 0.75, 1.5, 2.25 or 3 µg/kg. The pharmacodynamic response of PEGylated TPO Compound No. 1 was measured as elevation in platelet counts. PEGylated TPO Compound No. 1 levels were determined in platelet poor plasma using a validated enzyme-linked immunosorbent assay. Levels of endogenous TPO, EPO, IL-6 and IL-11 were measured at the indicated time points using standard immunoassays. A biosensor immunoassay (BiaCore technology) was used for measuring antibody formation against the peptide moiety of PEGylated TPO Compound No. 1. The effect on platelet function was measured by monitoring collagen-induced platelet aggregation at 4 hours and 12 days after PEGylated TPO Compound No. 1 administration.

Figure 7:
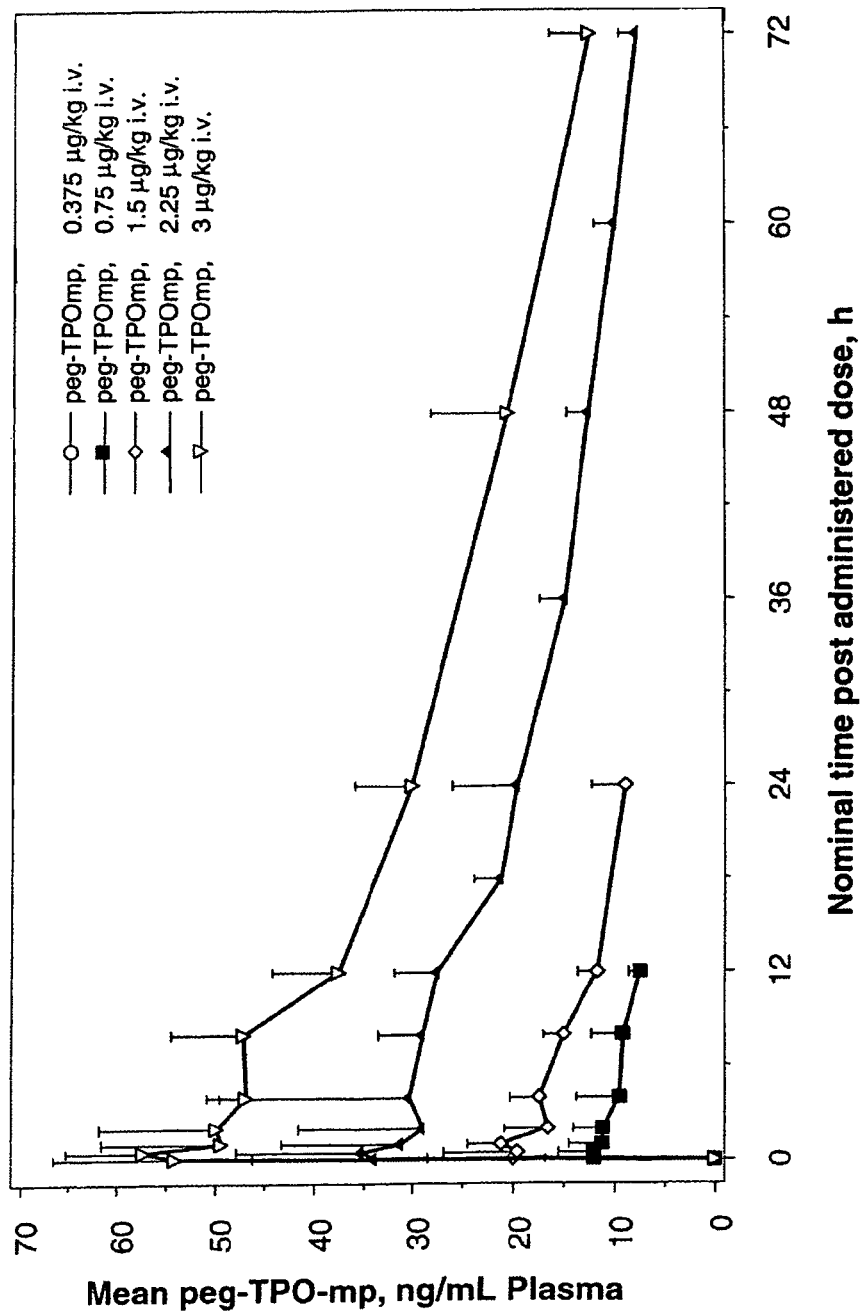
FIG. 7 shows the PK, concentration—time profiles of PEGylated TPO Compound No. 1 in healthy male volunteers: filled square—PEGylated TPO Compound No. 1, 0.75 μg/kg i.v.; open diamond—PEGylated TPO Compound No. 1, 1.5 μg/kg i.v.; filled upward-triangle—PEGylated TPO Compound No. 1, 2.25 μg/kg i.v.; open downward-triangle—PEGylated TPO Compound No. 1, 3 μg/kg i.v.

PK analysis indicated dose-related kinetics of PEGylated TPO Compound No. 1, although at doses of 0.75 µg/kg or lower, plasma concentrations of PEGylated TPO Compound No. 1 were generally below the limit of quantification of 6.25 ng/mL (FIG. 7). Four subjects in the 0.375 µg/kg dose group and one subject in the 3.0 µg/kg PEGylated TPO Compound No. 1 dose group had no quantifiable plasma levels. Mean $C_{max}$ values ranged from 10.9 ng/mL at 0.75 µg/kg PEGylated TPO Compound No. 1 to 61.7 ng/mL at 3.0 µg/kg PEGylated TPO Compound No. 1 (Table 1). No PK data could be measured at 0.375 µg/kg i.v. of TPO Compound No. 1. The mean terminal half-life of PEGylated TPO Compound No. 1 ranged from approximately 18 to 36 hours. The median $t_{max}$ ranged from 0.09 to 2 hours. The increase in $C_{max}$ with increasing dose was approximately dose proportional, but there was an apparent increase in the normalized $AUC_{0-24}$ value with increasing dose, suggesting a higher than dose proportional increase.

TABLE 1

Summary of PK analysis

| | Cmax (ng/mL) | $t_{1/2}$ (h) | $AUC_\infty$ (ng · h/mL) | $AUC_{0-24}$ (ng · h/mL) |
|---|---|---|---|---|
| | 0.75 µg/kg dose | | | |
| N | 6 | 1 | 0 | 0 |
| Mean | 10.9 | NQ | NQ | NQ |
| Min-Max | BLQ-18.8 | 18.6 | NQ | NQ |
| | 1.5 µg/kg dose | | | |
| N | 6 | 2 | 1 | 4 |
| Mean | 20.9 | NQ | NQ | 311 |
| Min-Max | 7.53-28.5 | 13.1-22.5 | 475 | 268-359 |
| | 2.25 µg/kg dose | | | |
| N | 6 | 2 | 3 | 4 |
| Mean | 39.7 | NQ | 1561 | 678 |
| Min-Max | 13.1-59.1 | 29.8-48.5 | 1551-1569 | 655-694 |
| | 3.0 µg/kg dose, excluding subject 1027 who had no quantification concentrations | | | |
| N | 6 | 4 | 3 | 5 |
| Mean | 61.7 | 36.1 | 2257 | 965 |
| Min-Max | 53.9-76.0 | 27.7-51.3 | 1773-2764 | 823-1124 |

Figure 8:
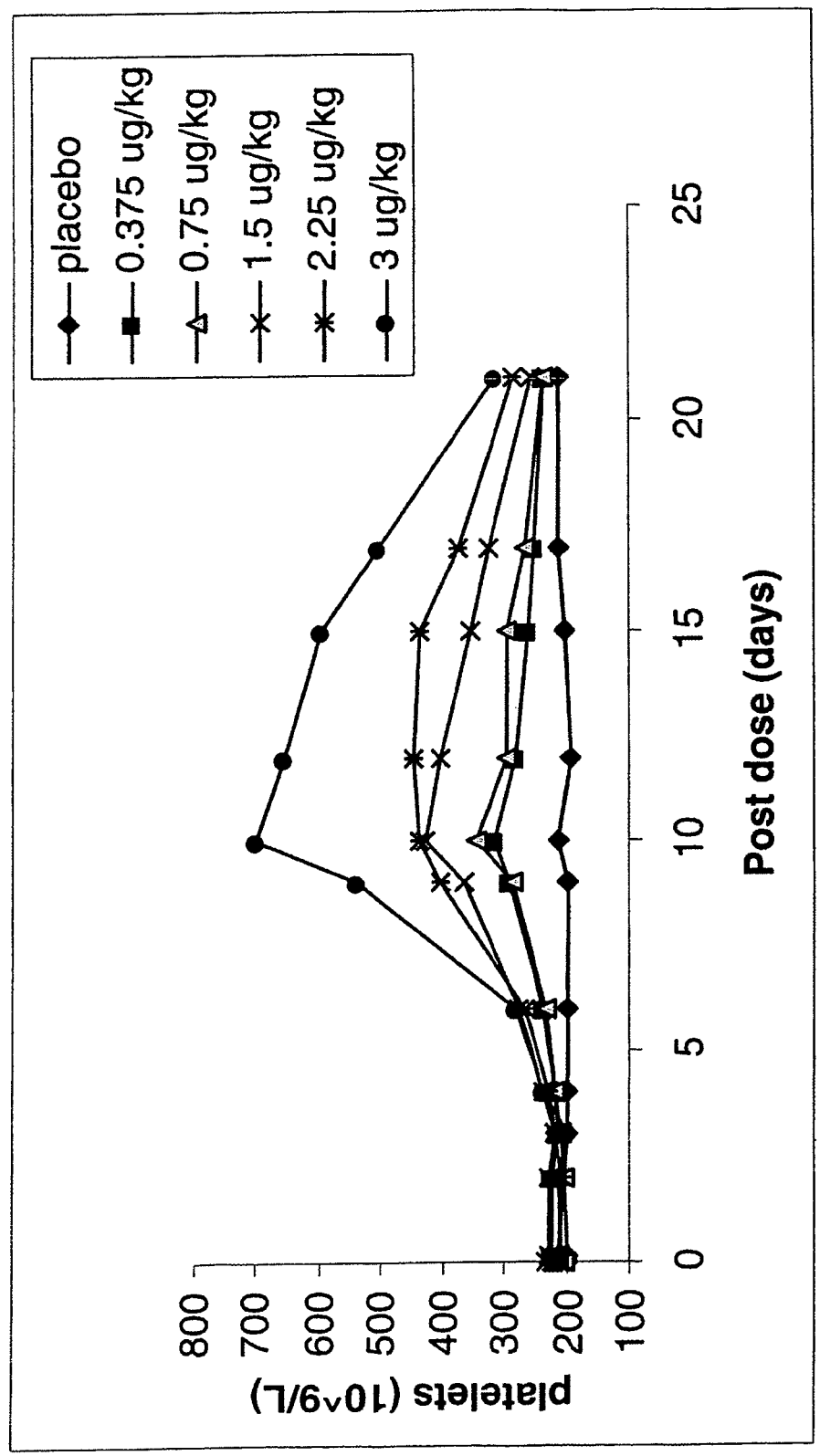
FIG. 8 shows that the platelet counts increased dose-dependently in healthy male volunteers post administration of PEGylated TPO Compound No. 1.

Platelet response to the administration of PEGylated TPO Compound No. 1 was similar to published results for rhTPO and AMG531. Platelet counts increased dose-dependently reaching peak levels at Day 10-12, and counts returned to baseline within 3-4 weeks (FIG. 8). Mean peak platelet counts ranged from $315 \times 10^9$/L at 0.375 µg/kg i.v. to $685 \times 10^9$/L at 3 µg/kg i.v., and mean maximal platelet counts increased from baseline ranged from 1.4-fold at 0.375 µg/kg to 3.2-fold at 3.0 µg/kg (Table 2). At least 50% increase in platelets was observed in 4 out 6 subjects receiving PEGylated TPO Compound No. 1 at a dose of 0.75 ug/kg, while at least 2-fold increase in platelet count was observed in about 3 out of 6 subjects at a dose of 1.5 ug/kg, etc. The dose of 0.75 ug/kg i.v. has been chosen as the starting dose for phase II clinical study.

Apart from changes in platelet counts, other mature circulating blood cells were not affected (data not shown). In addition, administration of PEGylated TPO Compound No. 1 did not affect platelet function, not at the time of administration, nor at 12 days post-dose, at the time of the appearance of newly produced platelets.

TABLE 2

Summary of platelet count analyses

| TPO Compound No. 1 | 0 (µg/kg) | 0.375 (µg/kg) | 0.75 (µg/kg) | 1.5 (µg/kg) | 2.25 (µg/kg) | 3.0 (µg/kg) |
|---|---|---|---|---|---|---|
| N | 10 | 6 | 6 | 6 | 6 | 6 |
| n (>1.5×) | 0 | 3 | 3 | 4 | 4 | 5 |
| n (>2×) | 0 | 0 | 1 | 3 | 4 | 5 |
| n (>3×) | 0 | 0 | 0 | 0 | 0 | 4 |
| n (>4×) | 0 | 0 | 0 | 0 | 0 | 1 |
| $Plt_0$ $(10^9/L)^{1)}$ | 192/203 (163-233) | 223/205 (159-304) | 212/212 (155-264) | 228/230 (200-258) | 215/203 (193-261) | 208/200 (150-284) |
| $Plt_{max}$ $(10^9/L)^{1)}$ | 230/225 (189-271) | 315/309 (214-482) | 347/335 (232-495) | 430/458 (238-597) | 454/500 (254-576) | 685/750 (188-979) |
| $Plt_{max}/Plt_0^{1)}$ | 1.14/1.13 (1.04-1.38) | 1.42/1.42 (1.08-1.81) | 1.63/1.63 (1.15-2.12) | 1.91/2.13 (1.01-2.59) | 2.15/2.33 (1.28-2.98) | 3.21/3.50 (1.25-4.52) |

Figure 9:
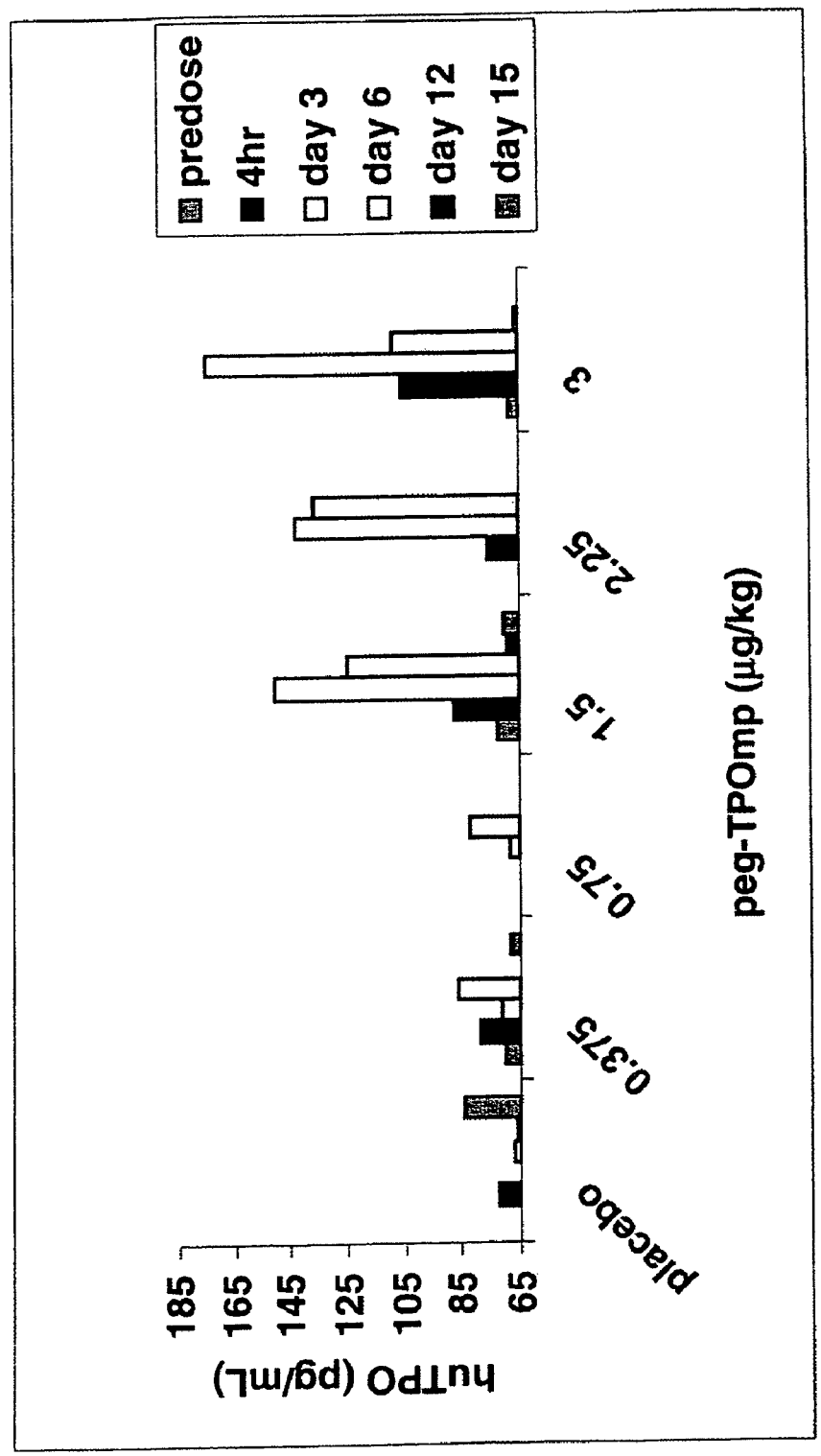
FIG. 9 shows that endogenous TPO levels increased dose-dependently in healthy male volunteers post administration of PEGylated TPO Compound No. 1.

The effect of PEGylated TPO Compound No. 1 administration on growth factors that are known to possess thrombopoietic activity was assessed. Endogenous TPO levels dose-dependently increased, reaching peak levels at 3 days post-dose (FIG. 9). No significant changes were observed in blood levels of IL-6, IL-11 and EPO levels.

Platelet function, assessed as collagen-induced platelet aggregation in whole blood, was not different between the treatments. None of the subjects experienced a serious adverse event or dose-limiting toxicities. The most frequently observed adverse events included mild headache and fatigue and occurred both after active treatment and placebo. No antibodies against PEGylated TPO Compound No. 1 were detected. These results indicate that PEGylated TPO Compound No. 1 was well tolerated at the tested dose range.

Although only preferred embodiments of the invention are specifically described above, it will be appreciated that modifications and variations of the invention are possible without departing from the spirit and intended scope of the invention.

What is claimed is:

1. A method for treating a patient suffering from thrombocytopenia, comprising administering to the patient a therapeutically effective dose or amount of a peptide compound comprising the following sequence: (H-IEGPTLRQ(2-Nal)LAARX$_{10}$)$_2$K-NH$_2$ wherein X$_{10}$ is sarcosine, wherein said peptide compound is covalently attached to polyethylene glycol, wherein said polyethylene glycol is monomethoxypolyethylene glycol (MePEG-OH).

2. The method of claim 1, wherein said peptide compound is administered at a dose range of between about 0.1 and about 5 μg/kg.

3. The method of claim 1, wherein said peptide compound is administered at a dose range of about 0.375, 0.75, 1.5, 2.25 or 3 μg/kg, respectively.

4. The method of claim 1, wherein administration of said peptide compound results in a mean $C_{max}$ value of about 10 ng/mL at about 0.75 μg/kg peptide compound.

5. The method of claim 1, wherein administration of said peptide compound results in a mean $C_{max}$ value of about 60 ng/mL at about 3.0 μg/kg peptide compound.

6. The method of claim 1, wherein administration of said peptide compound results in a mean terminal half-life of said peptide compound of from about 18 hours to about 36 hours.

7. The method of claim 1, wherein administration of said peptide compound results in a median $t_{max}$ of from about 0.09 hours to about 2 hours.

8. The method of claim 1, wherein administration of said peptide compound results in an about 50% increase in platelet count at a dose of about 0.75 μg/kg.

9. The method of claim 1, wherein administration of said peptide compound results in an about 2-fold increase in platelet count at a dose of greater than about 0.75 μg/kg.

10. The method of claim 1, wherein administration of said peptide compound results in an increase in endogenous TPO levels.

11. The method of claim 1, wherein said monomethoxypolyethylene glycol (MePEG-OH) has an average molecular weight of between about 500 to about 40,000 daltons.

12. The method of claim 11, wherein said monomethoxypolyethylene glycol (MePEG-OH) has an average molecular weight of between about 5,000 to about 20,000 daltons.

13. The method of claim 1, wherein each of the dimeric subunits of said peptide compound is covalently attached to polyethylene glycol, wherein said polyethylene glycol is monomethoxypolyethylene glycol (MePEG-OH).

\* \* \* \* \*